(12) United States Patent
Dotson

(10) Patent No.: US 7,479,136 B2
(45) Date of Patent: Jan. 20, 2009

(54) OPHTHALMIC PHOTOTHERAPY TREATMENT METHOD

(76) Inventor: Robert S. Dotson, 200 New York Ave., Suite 130, Oak Ridge, TN (US) 37830

( * ) Notice: Subject to any disclaimer, the term of this patent is extended or adjusted under 35 U.S.C. 154(b) by 2 days.

(21) Appl. No.: 11/858,351

(22) Filed: Sep. 20, 2007

(65) Prior Publication Data

US 2008/0009839 A1 Jan. 10, 2008

Related U.S. Application Data

(63) Continuation-in-part of application No. 11/106,416, filed on Apr. 14, 2005.

(51) Int. Cl.
*A61B 18/18* (2006.01)
(52) U.S. Cl. ............... 606/4; 606/3; 606/5; 607/88; 128/898
(58) Field of Classification Search ........... 606/3–5, 606/10; 607/88, 89; 128/898
See application file for complete search history.

(56) References Cited

U.S. PATENT DOCUMENTS

| | | | |
|---|---|---|---|
| 4,930,504 A | 6/1990 | Diamantopoulos et al. | |
| 5,259,380 A | 11/1993 | Mendes et al. | |
| 5,290,272 A * | 3/1994 | Burstein et al. | 606/4 |
| 5,533,997 A * | 7/1996 | Ruiz | 606/5 |
| 5,683,436 A | 11/1997 | Mendes et al. | |
| 5,755,752 A | 5/1998 | Segal | |
| 5,766,233 A | 6/1998 | Thiberg | |
| 5,964,749 A | 10/1999 | Eckhouse et al. | |
| 6,019,754 A * | 2/2000 | Kawesch | 606/4 |
| 6,238,424 B1 | 5/2001 | Thiberg | |
| 6,274,614 B1 | 8/2001 | Richter et al. | |
| 6,287,296 B1 | 9/2001 | Seiler et al. | |
| 6,387,089 B1 | 5/2002 | Kreindel et al. | |
| 6,443,978 B1 | 9/2002 | Zharov | |
| 6,471,716 B1 | 10/2002 | Pecukonis | |
| 6,537,302 B1 | 3/2003 | Thiberg | |
| 6,607,522 B1 * | 8/2003 | Hamblin et al. | 606/8 |
| 6,677,366 B2 | 1/2004 | Richter et al. | |
| 6,689,124 B1 | 2/2004 | Thiberg | |
| 6,811,563 B2 | 11/2004 | Savage, Jr. et al. | |
| 7,014,639 B2 | 3/2006 | Walneck et al. | |
| 7,118,563 B2 | 10/2006 | Weckwerth et al. | |
| 2002/0004673 A1 | 1/2002 | Cho et al. | |
| 2002/0087207 A1 | 7/2002 | Cho et al. | |
| 2003/0050674 A1 | 3/2003 | Joshi | |
| 2003/0093135 A1 | 5/2003 | Denton et al. | |

OTHER PUBLICATIONS

Nadine Tosk, "FDA Clears GentleWaves®—The First and Only Light Emitting Diode Device for the Treatment of Periorbital Wrinkles and Rhytids", Company News Release, Jan. 14, 2005, 2 pg., LightBio Science, Virginia Beach, Virginia.
Lightbioscience, LLC, "GentleWaves® LED Photomodulation Device," internet, Mar. 1, 2005, 1 pg., LightBio Science, Virginia Beach, Virginia, www.lightbioscience.com/led_device.html.
Meidspa Financing, New & Noteworthy MedSpa Equipment/Robotic LED Skin Rejuvenation/FLIP4, internet, Mar. 1, 2005, 1 pg., www.medspafinancing.com/new.html.
Jennifer Brodeur, FLIP4, internet, Mar. 1, 2005, 1 pg., www.spatrends.com/index.

* cited by examiner

*Primary Examiner*—Ahmed M Farah
(74) *Attorney, Agent, or Firm*—Pitts & Brittian, P.C.

(57) ABSTRACT

An ophthalmic phototherapy device (10) and associated phototherapy treatment method for promoting healing of damaged or diseased eye tissue. The ophthalmic phototherapy device (10) includes a light emitting mechanism (12) for transmitting light of at least one preselected wavelength to the eye tissue, whereby the light transmitted to the damaged or diseased eye tissue stimulates activity in the eye tissue to promote healing. The ophthalmic phototherapy method includes exposing the damaged or diseased eye tissue to light of at least one wavelength for a selected period of time.

15 Claims, 4 Drawing Sheets

US 7,479,136 B2

OPHTHALMIC PHOTOTHERAPY TREATMENT METHOD

CROSS-REFERENCE TO RELATED APPLICATIONS

This application is a Continuation-In-Part of U.S. application Ser. No. 11/106,416, filed Apr. 14, 2005.

STATEMENT REGARDING FEDERALLY SPONSORED RESEARCH OR DEVELOPMENT

Not Applicable

BACKGROUND OF THE INVENTION

1. Field of Invention

This invention relates to an ophthalmic phototherapy device and an associated treatment method. More specifically, the present invention is related to a device which produces light within a preselected frequency range for being directed into the eye of a patient, and a related treatment method for promoting the healing of damaged or diseased eye tissue.

2. Description of the Related Art

It is well known that exposure of animal tissue to light can be used to modulate the activity of such biologic tissue. In this regard, exposing biologic tissue to different wavelengths of light, commonly referred to as light therapy or phototherapy, acts on different mechanisms within individual cells to promote healing and cellular rejuvenation. Accordingly, phototherapy has been utilized to treat infants for jaundice (e.g., U.S. Pat. No. 6,811,563), to treat acne and other skin conditions (e.g., U.S. Pat. No. 6,387,089), to treat rhinitis (e.g., U.S. Pat. No. 5,683,436), and to treat traumatic tissue injuries (e.g. U.S. Pat. No. 6,471,716). With respect to specific wavelengths utilized for phototherapy, and their known effects, light in the yellow range (approximately 577 nm to 597 nm) has be shown to switch off collagenase production by down-regulating MMPs and switching on new collagen production. In this regard, collagenases are enzymes that break down the native collagen that holds animal tissue together. Light in the red range (approximately 640 nm to 700 nm) has been shown to decrease inflammation in injured tissue, increase ATP production, and otherwise stimulate beneficial cellular activity. Light in the blue range (approximately 405 nm to 450 nm) has been shown to kill the propionibacterium that causes acne by activating the porphyrins produced by the bacteria.

Several commercial phototherapy devices are available including devices which utilize light-emitting diodes, or LEDs. Two such devices are the Gentlewaves® LED Photomodulation Device manufactured by Light BioScience, LLC, which includes a panel of LEDs for treating skin conditions, and the Flip4 Max7 LED device which incorporates an LED panel capable of producing multiple wavelengths of light, and which is also marketed for treating skin conditions. Further, the U.S. military and NASA have utilized small hand-held devices incorporating LED arrays that are used to reduce inflammation and promote healing. This notwithstanding, phototherapy is not in use for the purpose of promoting the healing of damaged or diseased eye tissue within the field of ophthalmology. A phototherapy device using LEDs has been utilized in an effort to strengthen corneal tissue. However, this device utilizes LEDs in the ultraviolet range to induce cross-linking of corneal collagen and, thereby, stiffen the cornea. Thus, this process, in effect, ages the tissue, as opposed to facilitating the production of new, "normal" tissue. Therefore, the process is not one in which healing of tissue is promoted.

Various phototherapy devices and procedures are disclosed in U.S. Pat. Nos. 6,677,366; 6,689,124; 6,537,302; 6,443,978; 6,287,296; 6,274,614; 6,238,424; 5,964,749; 5,766,233; 5,259,380; and 4,930,504. Other devices and procedures are disclosed in U.S. Patent Application Pub. Nos. 2003/0093135; 2003/0050674; 2002/0087207; and 2002/0004673.

BRIEF SUMMARY OF THE INVENTION

The present invention provides an ophthalmic phototherapy device, and an associated phototherapy method, for promoting healing of damaged or diseased eye tissue. The ophthalmic phototherapy device includes a light emitting mechanism for transmitting light of at least one preselected wavelength to the damaged or diseased eye tissue, whereby the light transmitted to the eye tissue stimulates activity in the eye tissue to promote healing. The light emitting mechanism can include a light panel having a plurality of light emitting diodes (LEDs) for emitting light. In one embodiment the device has a first set of LEDs capable of emitting light having a first wavelength, and at least a second set of LEDs capable of emitting light having a second wavelength. Further, a controller is provided for selectively controlling which LEDs are energized at any given time, such that different sequences and/or combinations of light wavelengths can be selectively communicated to the eye tissue being treated.

The ophthalmic phototherapy method of the present invention includes exposing the damaged or diseased eye tissue to light of at least one preselected wavelength for a preselected period of time to stimulate cellular activity that promotes healing. Further, in one application of the method the tissue is exposed to light of a plurality of wavelengths either sequentially, or in combination.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
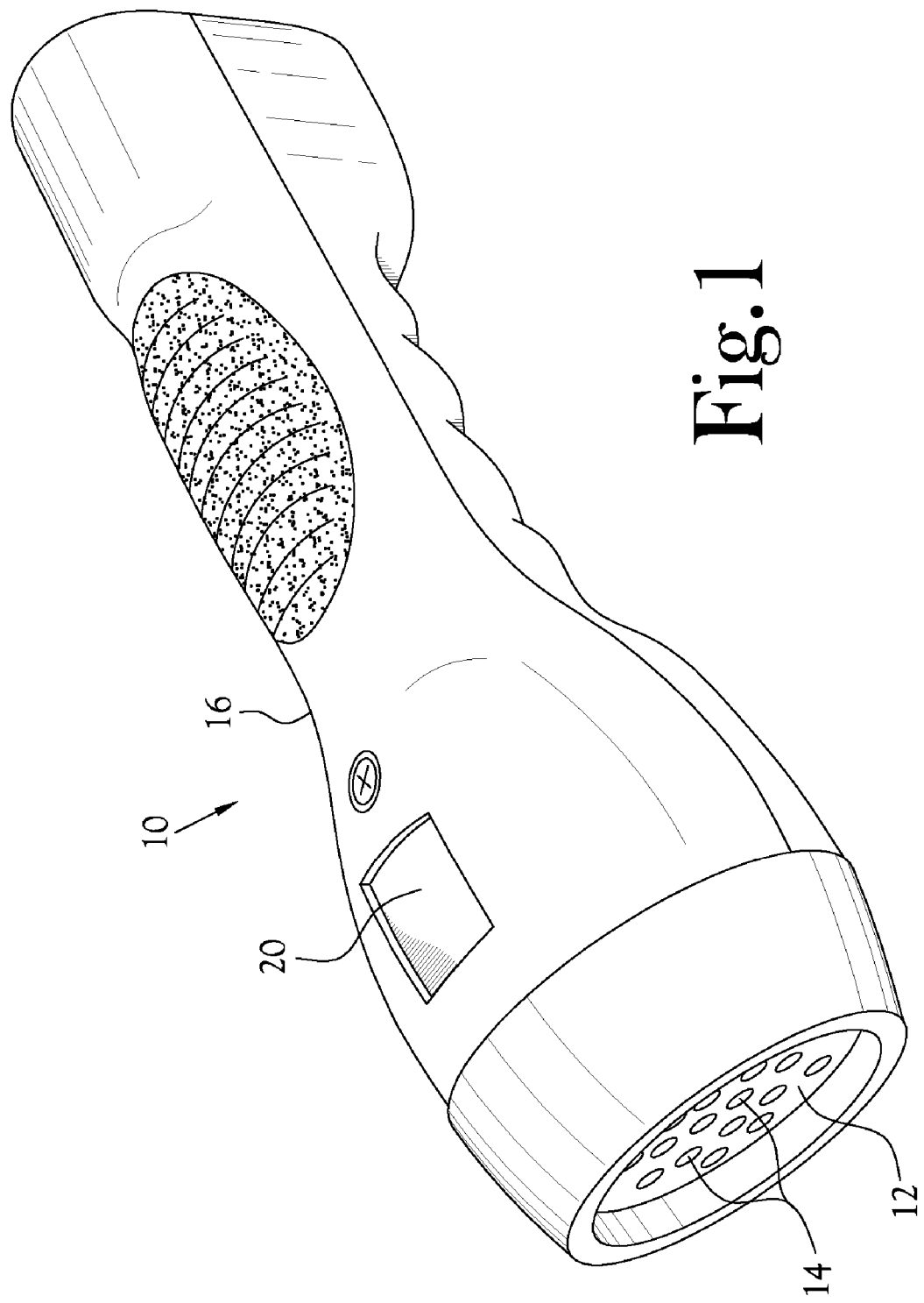
FIG. 1 is a perspective view of an ophthalmic phototherapy device of the present invention.

An ophthalmic phototherapy device of the present invention is illustrated generally at 10 in the drawings. As will be discussed in detail below, the phototherapy device 10 produces light of a selected wavelength, or produces selected sequences or combinations of light having differing wavelengths within a particular range of wavelengths. In accordance with the ophthalmic treatment method of the present invention, the light emitted by the phototherapy device 10 is directed into the eye of a patient to promote healing of damaged or diseased eye tissue.

Figure 2:
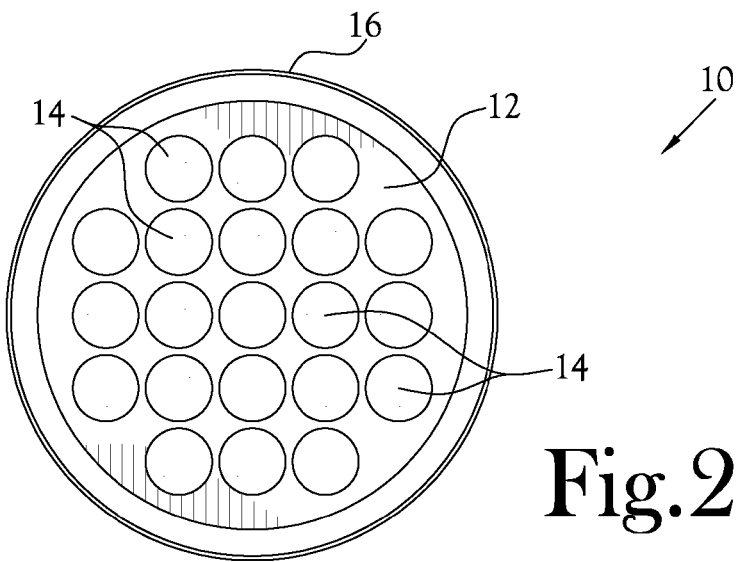
FIG. 2 is a front elevation view of an ophthalmic phototherapy device of the present invention.

The ophthalmic phototherapy device of the present invention can be variously configured to be either hand-held, or mounted on an operatively associated medical device or other supporting structure. For example, the ophthalmic phototherapy device 10 illustrated in FIGS. 1 and 2 is configured to facilitate hand-held use of the device 10. In the illustrated embodiment the device 10 incorporates a light emitting mechanism that includes a light panel 12 incorporating a plurality of light emitting diodes or LEDs 14. However, those skilled in the art will recognize that various mechanisms which are capable of emitting light of a desired wavelength could be used, and the LEDs 14 are merely one mechanism for producing the desired light. For example, the light emitting mechanism could include a low power laser source for generating light of the appropriate wavelength(s), or one or more filtered incandescent or fluorescent lights.

With respect to the particular LEDs used in the panel 12, and as will be discussed further below, one approximate range of wavelengths desirable for ophthalmic phototherapy is between 810 nm and 490 nm. However, other wavelengths may be beneficial for certain applications. Thus, depending on the particular therapeutic application, the panel 12 can be configured to have a plurality of LEDs 14 that produce the same wavelength of light within a desired range, or the panel 12 can incorporate selected combinations of LEDs 14 capable of producing light of differing wavelengths within a desired range. As will be discussed further below, where selected combinations of LEDs 14 are used which produce different wavelengths, the operator of the device 10 can select among wavelengths to be emitted within a desired range. Alternatively, where the ability to select between the wavelengths of the light emitted is desired, the panel 12 could incorporate LEDs 14 that produce a common wavelength and conventional filters (not shown) could be used to alter the wavelength to that desired.

Figure 5:
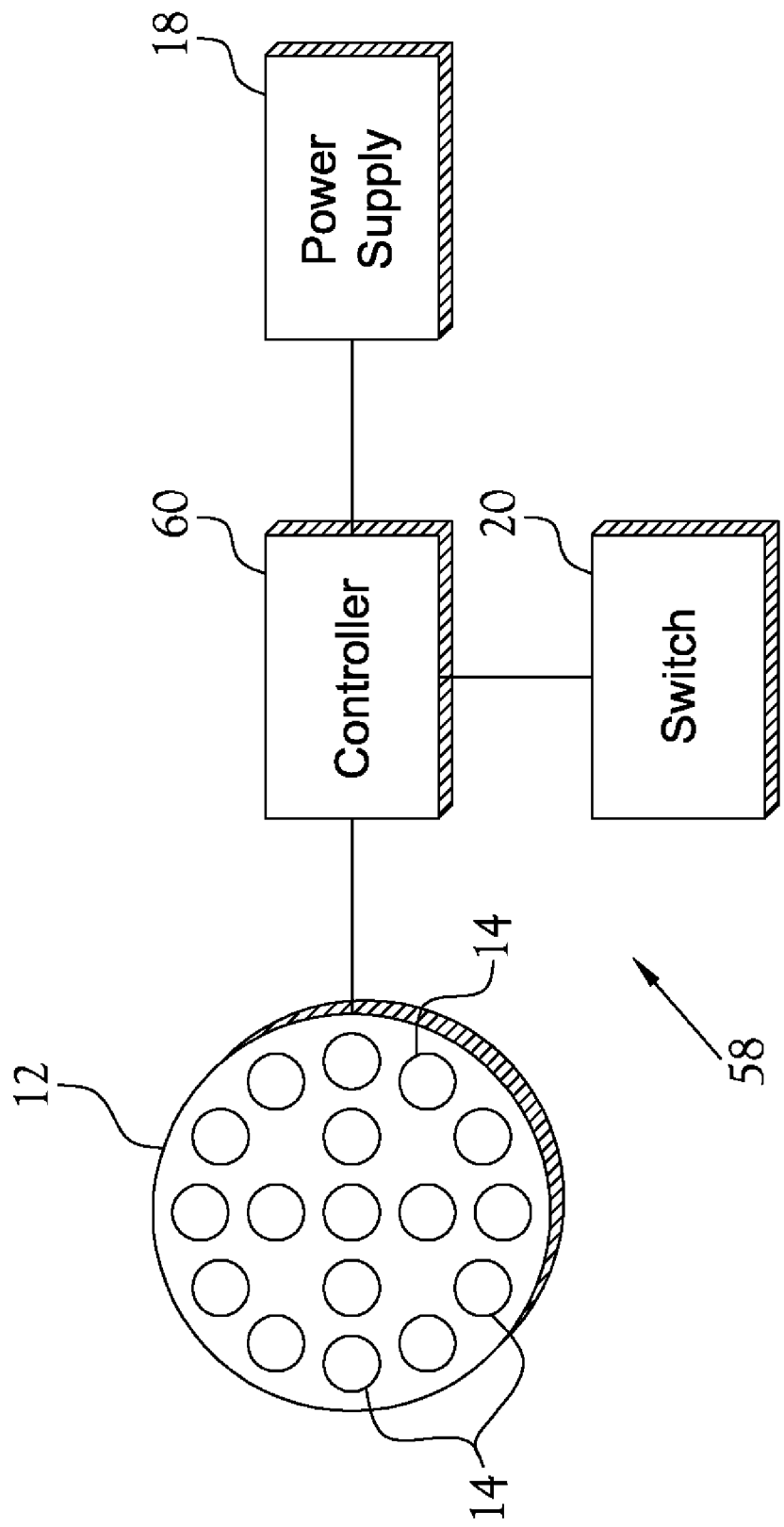
FIG. 5 is a block diagram of a power/control system for an ophthalmic phototherapy device of the present invention.

As illustrated in FIG. 1, the panel 12 is mounted in a housing 16 that is configured to be held in one's hand to facilitate use of the device 10. As schematically illustrated in FIG. 5, the device 10 is provided with a power supply 18 for energizing the panel 12 in order to selectively emit light. In the embodiment of FIG. 1 the power supply could be a battery (not shown) that is preferably rechargeable, but it will be understood that suitable circuitry could be provided for connecting the device to a conventional AC power supply such as a wall outlet. Further, the device 10 is provided with a suitable switch 20 for selectively turning the panel 12 on and off.

Figure 3:
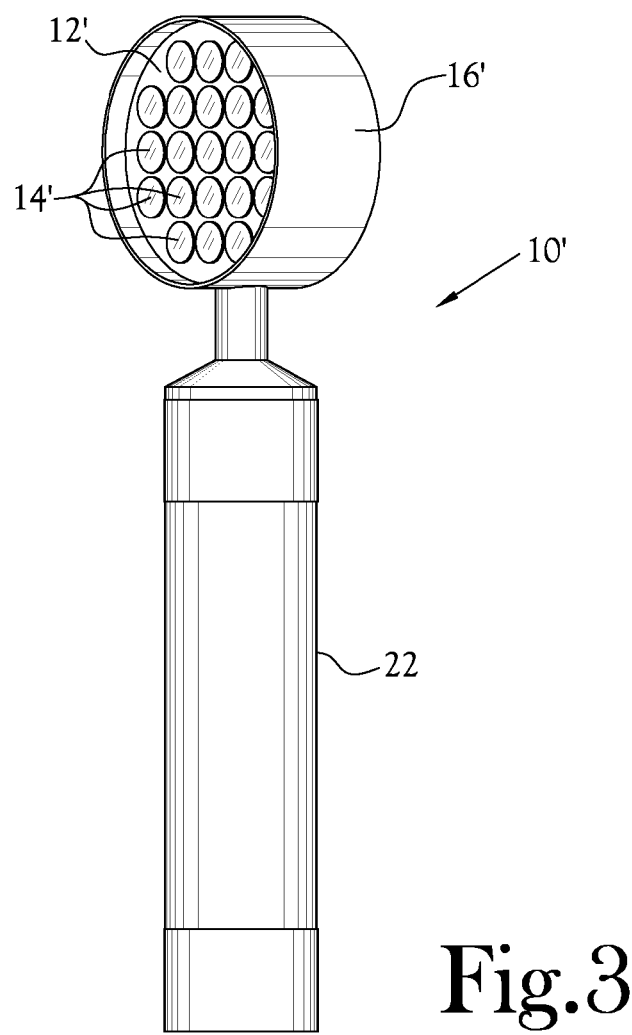
FIG. 3 is a perspective view of an alternated embodiment of an ophthalmic phototherapy device of the present invention.

In FIG. 3 an alternate embodiment of the ophthalmic phototherapy device of the present invention is illustrated at 10'. It will be noted that features of the device 10' that are common to the device 10 are referenced with common prime numerals. Those skilled in the art will recognize that certain hand-held ophthalmic instruments, such as retinoscopes and ophthalmoscopes, utilize interchangeable, detachable handles which incorporate rechargeable batteries. The ophthalmic phototherapy device 10' includes a housing 16' that detachably couples with such an interchangeable, rechargeable battery handle 22. Thus, the device 10' utilizes a power supply which is commonly available to ophthalmic health care professionals, and does not require a recharging system that is unique to the phototherapy device.

Figure 4:
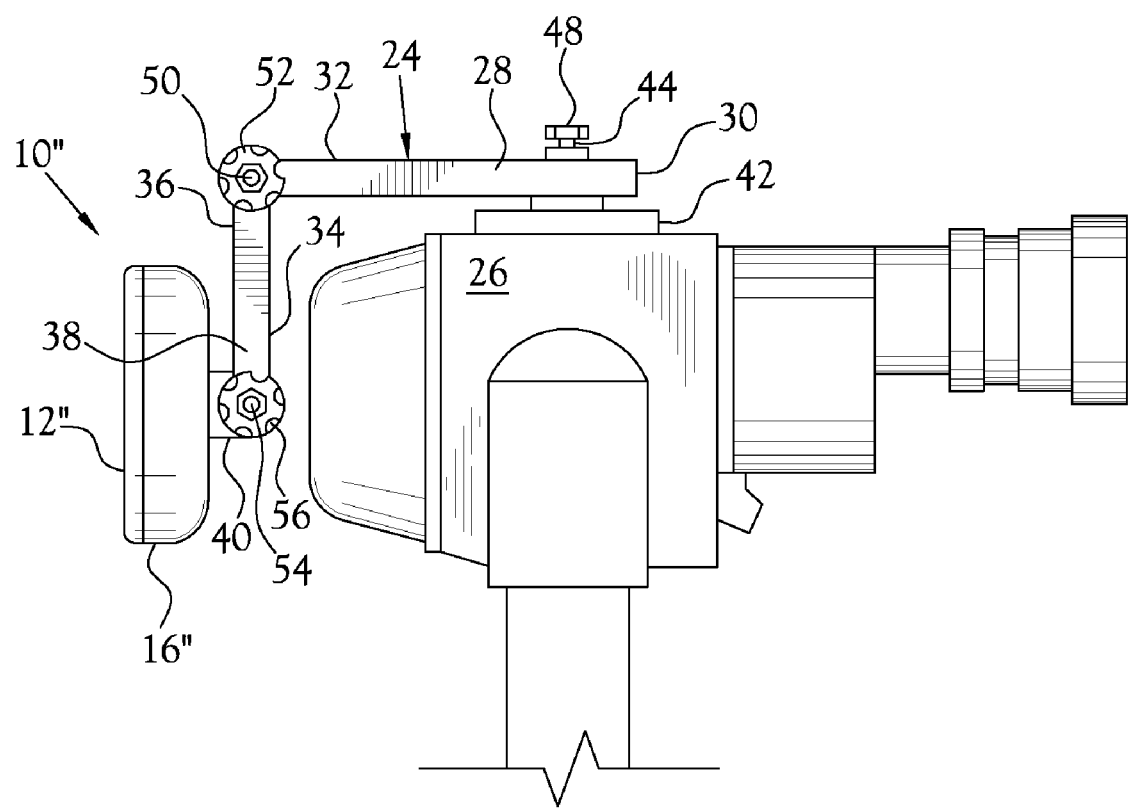
FIG. 4 is a side elevation view of a further alternate embodiment of an ophthalmic phototherapy device of the present invention mounted on a slit lamp.

A further alternate embodiment of the ophthalmic phototherapy device of the present invention is illustrated at 10" in FIG. 4. In this regard, it will be noted that features of the device 10" that are common to the device 10 are referenced with common double prime numerals. As illustrated, the ophthalmic phototherapy device 10" includes an articulated arm 24 that allows the device 10" to be adjustably mounted on a piece of operatively associated ophthalmic equipment such as the illustrated slit lamp 26. Although, the device 10" is illustrated as being mounted on a slit lamp 26 in FIG. 4, it will be understood that the device 10" could be mounted on various other pieces of equipment or structures. For example, and as will be discussed further below, in one embodiment, the device 10" is mounted proximate the head of an excimer laser such that device 10" can be utilized immediately before, during and/or after laser eye surgery.

Whereas the articulated support arm 24 could define various jointed configurations which allow the device 10" to be selectively positioned at various locations while being supported on associated ophthalmic equipment or other structures, the illustrated arm 24 includes a first arm section 28 having first and second end portions 30 and 32, respectively. The first end portion 30 is pivotally secured to the slit lamp 26 or other supporting structure, such that the arm 24 can be selectively pivoted in a substantially horizontal plane. The second end portion 32 of the first arm section 28 is pivotally secured to the first end portion 36 of a second arm section 34 such that the second arm section 34 pivots in a substantially vertical plane. Further, the second arm section 34 is pivotally secured proximate its second end portion 38 to a bracket 40 provided on the housing 16" such that the housing 16" and the light panel 12" pivot in a substantially vertical plane which is substantially perpendicular to the plane in which the second arm section 34 pivots.

It will be recognized that various mechanisms could be used for pivotally securing the first arm section 28 to a supporting structure, for pivotally securing the first arm section 28 to the second arm section 34, and for pivotally securing the second arm section 34 to the bracket 40. However, as illustrated in FIG. 4, in one embodiment an attachment structure 42 is provided that is secured to the supporting structure, as by an adhesive or by mechanical fasteners (not shown), and a threaded fastener 44 having a locking knob 48 is used to pivotally, and lockably, secure the first end portion 30 of the first arm section 28 to the attachment structure 42. A second threaded fastener 50 having a locking knob 52 is provided for pivotally, and lockably, securing the second arm section 34 to the first arm section 28, and a third threaded fastener 54, with a locking knob 56, is provided for pivotally, and lockably, securing the second arm section 34 to the bracket 40. Thus, it will be recognized that the articulated support arm 24 allows the light panel 12" to be pivoted to a position where it does not interfere with the use of the equipment on which it is mounted, and allows the light panel 12" to be pivoted into position to emit light into the eye of a patient when needed. Whereas the ophthalmic phototherapy device 10 and device 10' could be used in conjunction with laser eye surgery, it will be recognized that use of the device 10" with its articulated support arm 24 is particularly advantageous. In this regard, the articulated support arm 24 allows the device 10" to be mounted proximate a laser surgery apparatus such that both immediately prior to and immediately following the surgical procedure, the panel 12 can be rotated into position to emit light into the eye to promote healing.

As will be discussed below with respect to the phototherapy method of the present invention, it may be advantageous to control the wavelength of the light emitted by the device 10, the duration of a patient's exposure to the light emitted, and/or the brightness of the light emitted. Accordingly, as illustrated in FIG. 5, one embodiment the ophthalmic phototherapy device 10 includes a power/control system 58 that includes a controller 60 that can include a timer for automatically turning the LED's on and/or automatically turning the LEDs off after a preselected period of time. The controller 60 can also include circuitry for controlling the brightness of the LEDs 14, and, where LEDs 14 which emit light of different wavelengths are used, circuitry for preselecting which LEDs are lit at any given time. Further, it is contemplated that the controller 60 could include a microprocessor to control these various functions, and to allow different LEDs to be lit in a desired sequence, or in a pulsed format.

As set forth above, the phototherapy method of the present invention includes exposing tissue of the eye to light of a preselected wavelength to promote healing of the eye tissue. The approximate range of wavelengths desirable for ophthalmic phototherapy correspond to portions of the visible and invisible infrared spectrum ranging from blue light to near-infrared and infrared light, in other words, light having wavelengths between approximately 490 nm and 1000 nm, and preferably between 490 nm and 810 nm. However, wavelengths outside of this range may be helpful for certain treatment applications. In this regard, the wavelength used will vary depending on the injury or eye condition being treated. For example, 590 nm directed into the eye is often beneficial for treating corneal trauma. In this regard, light in the yellow range (approximately 577 nm to 597 nm) switches off collagenase production by down-regulating MMPs and switches on new collagen production. Red light (approximately 640-700 nm) is often effective in decreasing inflammation of tissue in the eye, increasing ATP production, and resetting cells to become more normal. Further, a preselected sequence or combination of wavelengths can be advantageously used for some conditions. For example, a sequence or combination of infrared or near-infrared light, red light, and yellow light directed into the eye may be beneficial for treating glaucoma. The light stimulates the cells in the trabecular meshwork to produce macrophages that then reduce the pigment cells clogging the meshwork/drain of the eye.

The duration of the phototherapy treatments will vary depending on the particular eye condition being treated. In this regard, beneficial tissue response can be obtained from dosages of less than 4 joules/sq. cm, such that the duration of treatment can be relatively short. For example, to achieve approximate dosages of less than 4 joules/sq. cm, treatment duration could vary between under a minute to approximately 10 minutes. Further, although phototherapy treatments having durations of 40 seconds or less have been shown to be beneficial, longer treatments may be desirable to provide additional benefit.

In one application of the phototherapy method of the present invention the method is utilized to promote healing of eye tissue subsequent to a laser-assisted in situ keratomileusis procedure, commonly referred to as LASIK eye surgery. As will be understood by those skilled in the art, during LASIK surgery a knife, referred to as a microkeratome, is used to cut a flap in the epithelium of the cornea of an eye. Alternatively a laser, such as the InteraLase™ femtosecond (1054 nm) laser, can be used to cut the flap. Tissue is left uncut at one end of the flap to provide a hinge that allows the flap to be folded back to reveal the stroma, or middle section of the cornea. Pulses from a computer controlled excimer laser are then used to vaporize a portion of the stroma to facilitate the reshaping of the cornea. The flap of epithelium tissue is then replaced.

In accordance with one embodiment of the method of the present invention, light of a first preselected wavelength is directed into the patient's eye prior to laser surgery of the epithelium and stroma of the eye in order to promote healing and to suppress inflammation of the eye tissue. In more discreet embodiments, the light directed into the patient's eye prior to laser surgery is preselected to suppress inflammation of the eye tissue during and after surgery, and preferably exhibits a wavelength between the range of 640 nm and 1000 nm. Thereafter, laser surgery of the epithelium and stroma portions of the cornea of the eye is performed. Subsequent to the replacement of the flap of epithelial corneal tissue, light of a second preselected wavelength is directed into the patient's eye, illuminating the surgically damaged tissue, in order to promote healing and to suppress inflammation of the eye tissue.

Whereas other wavelengths may be beneficial, the yellow range of wavelengths (approximately 577 nm to 597 nm) is particularly beneficial for promoting the healing of eye tissue after laser eye surgery. Thus, in one embodiment, the light directed into the patient's eye subsequent to replacement of the epithelial flap is preselected to exhibit a wavelength between the range of approximately 577 nm and 1000 nm. Light in the red, wavelengths (approximately 640 nm to 700 nm) is particularly beneficial for limiting inflammation, increasing ATP production, and otherwise stimulating beneficial cellular activity. Thus, in more discreet embodiments, the light directed into the patient's eye prior to laser surgery is preselected to exhibit a wavelength between the range of approximately 640 nm to 700 nm, while the light directed into the patient's eye subsequent to laser surgery is preselected to exhibit multiple wavelengths in the ranges of between approximately 577 nm to 597 nm, and between approximately 640 nm to 700 nm.

In another embodiment of the method of the present invention, the application of light of the first preselected wavelength into the patient's eye prior to laser surgery of the epithelium and stroma of the eye is omitted. In this embodiment, light of a preselected wavelength is directed into the patient's eye subsequent to the replacement of the flap of corneal tissue illuminating the surgically damaged tissue of the epithelium and stroma of the eye in order to promote healing and/or suppress inflammation of the damaged eye tissue.

The length of time the damaged tissue is exposed to the light can vary. Exposure times of less than one minute can be beneficial, with exposure times in excess of 10 minutes being contemplated. It will be noted that use of the ophthalmic phototherapy device 10", with its articulated support arm 24, can be particularly useful in applying phototherapy in accordance with the present method subsequent to laser eye surgery. In this regard, the articulated support arm 24 allows the panel 12" to be rotated into position to emit light into the patient's eye immediately upon completion of the surgical procedure.

The phototherapy method of the present invention can also be beneficially used to promote healing of eye tissue in connection with various other surgical procedures. For example, the method can be used to promote healing in connection with LASEK or Epi-Lasik procedures, corneal inlays, corneal transplants (penetrating keratoplasty or PKP), cataract and intraocular implant (IOL) surgery, and glaucoma surgery. Utilized during or after such procedures, the present phototherapy method reduces healing time, and can reduce the need for extended use postoperative drugs such as steroids.

In light of the above, it will be recognized that the ophthalmic phototherapy devices 10, 10', and 10" of the present invention provide devices that are particularly well suited for administering phototherapy to the eye of a patient. Moreover, the phototherapy method of the present invention can be utilized to promote the healing of damaged eye tissue whether the damage is the result of disease, accident, or surgery. While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

The invention claimed is:

1. An ophthalmic phototherapy method for promoting the healing of eye tissue, said method comprising the steps of:
   a. discouraging inflammation in the portion of eye tissue by exposing a portion of eye tissue in an eye to light of at least a first wavelength for a first selected period of time;
   b. allowing the eye tissue to become damaged; and
   c. discouraging collagenase production and encouraging new collagen production in cells in the damaged eye tissue by exposing the damaged eye tissue to light of at least a second wavelength for a second selected period of time.

2. The ophthalmic phototherapy method of claim 1, wherein said step of allowing the eye tissue to become damaged includes performing laser eye surgery on the eye, thereby damaging the cornea of the eye.

3. The ophthalmic phototherapy method of claim 1 wherein each of the first and second wavelengths is between approximately 490 nm and approximately 1000 nm.

4. The ophthalmic phototherapy method of claim 1, said step of exposing the damaged eye tissue to a light of at least a second wavelength includes exposing the damaged eye tissue to light of a second wavelength and to light of at least a third wavelength.

5. The ophthalmic phototherapy method of claim 4 wherein the second wavelength is between approximately 577 nm and approximately 597 nm, and wherein the third wavelength is between approximately 640 nm and approximately 700 nm.

6. The ophthalmic phototherapy method of claim 1, further including the step of further discouraging inflammation in the portion of eye tissue by exposing the damaged eye tissue to light of at least a third wavelength for a second selected period of time.

7. The ophthalmic phototherapy method of claim 6 wherein said further discouragement of inflammation in the damaged eye tissue is accomplished by exposing the damaged eye tissue to a combination of light of the second wavelength and light of the third wavelength for said second selected period of time.

8. An ophthalmic phototherapy method for promoting the healing of damaged eye tissue subsequent to laser eye surgery, said method comprising the steps of:
   a. modulating the biological activity of cells in at least a portion of eye tissue in an eye by exposing the eye tissue to light of at least a first selected wavelength for a first selected period of time prior to the laser eye surgery;
   b. performing the laser eye surgery, thereby allowing the eye tissue to become damaged; and
   c. further modulating the biological activity of the cells of the damaged eye tissue by exposing the damaged eye tissue to a light of at least a second selected wavelength for a second selected period of time upon completion of the laser eye surgery.

9. The ophthalmic phototherapy method of claim 8 wherein said method includes exposing the damaged eye tissue to light of at least a second wavelength, and light of at least a third wavelength.

10. The ophthalmic phototherapy method of claim 8, wherein said first selected wavelength and said second selected wavelength are of approximately equal measurement.

11. An ophthalmic phototherapy method for promoting the healing of damaged eye tissue subsequent to laser eye surgery, said method utilizing an ophthalmic phototherapy device including a light panel having a plurality of LEDs for communicating light to the damaged eye tissue, said method comprising the steps of:
   a. modulating the biological activity of cells in at least a portion of eye tissue in an eye by exposing the eye tissue to light of at least a first selected wavelength for a first selected period of time prior to the laser eye surgery;
   b. cutting a flap in the cornea of the eye and folding back the flap to reveal the stroma of the cornea;
   c. using a laser to vaporize a portion of the stroma to facilitate the reshaping of the cornea;
   d. replacing the flap; and
   e. further modulating the biological activity of the cells of the damaged eye tissue by exposing the damaged eye tissue to a light of at least a second selected wavelength for a second selected period of time upon completion of the laser eye surgery.

12. The ophthalmic phototherapy method of claim 11 wherein each of the first and second wavelengths is between approximately 490 nm and approximately 1000 nm.

13. The ophthalmic phototherapy method of claim 11, said step of exposing the damaged eye tissue to a light of at least a second wavelength includes exposing the damaged eye tissue to light of a second wavelength and to light of at least a third wavelength.

14. The ophthalmic phototherapy method of claim 13 wherein the second wavelength is between approximately 577 nm and approximately 597 nm, and wherein the third wavelength is between approximately 640 nm and approximately 700 nm.

15. The ophthalmic phototherapy method of claim 13 wherein the damaged eye tissue is exposed to light of the second wavelength and subsequently exposed to light of the at least one third wavelength.

* * * * *